(12) United States Patent
Tran et al.

(10) Patent No.: US 7,892,248 B2
(45) Date of Patent: Feb. 22, 2011

(54) OCCLUSIVE CINCHING DEVICES AND METHODS OF USE

(75) Inventors: Tri Tran, Fremont, CA (US); Kim Nguyen, San Jose, CA (US); Hanh Ho, San Jose, CA (US); My Doan, San Jose, CA (US); Richard Murphy, Sunnyvale, CA (US); Michael P Wallace, Fremont, CA (US); Clifford Teoh, Los Altos, CA (US)

(73) Assignee: Stryker NV Operations Limited, Limerick (IE)

( * ) Notice: Subject to any disclaimer, the term of this patent is extended or adjusted under 35 U.S.C. 154(b) by 885 days.

(21) Appl. No.: 11/748,221

(22) Filed: May 14, 2007

(65) Prior Publication Data

US 2007/0213764 A1 Sep. 13, 2007

Related U.S. Application Data

(63) Continuation of application No. 10/338,514, filed on Jan. 7, 2003, now Pat. No. 7,229,454.

(51) Int. Cl.
*A61B 17/08* (2006.01)
(52) U.S. Cl. ...................................... 606/157
(58) Field of Classification Search ................ 606/113, 606/114, 127, 151, 153, 157, 200
See application file for complete search history.

(56) References Cited

U.S. PATENT DOCUMENTS

| | | | |
|---|---|---|---|
| 4,710,192 A | 12/1987 | Liotta et al. | |
| 4,923,464 A | 5/1990 | DiPisa, Jr. | |
| 5,122,136 A | 6/1992 | Gugliemi et al. | |
| 5,354,295 A | 10/1994 | Gugliemi et al. | |

(Continued)

FOREIGN PATENT DOCUMENTS

WO WO 99/02093 1/1999

(Continued)

OTHER PUBLICATIONS

Bhupender S. Gupta, "Medical Textile Structure: An Overview" Medical Plastics and Biomaterials, MPB Archive, Jan. 1998.

*Primary Examiner*—Kevin T Truong
(74) *Attorney, Agent, or Firm*—Vista IP Law Group LLP

(57) ABSTRACT

Methods and devices for blocking orifices and occluding cavities within a patient are provided. The device in one variation comprises first and second tubular members attached to a collapsible sealing element. The device can be placed through an orifice and the collapsible sealing element can be collapsed to seal the orifice. An embolic may be introduced distal to the sealing element to occlude a cavity. The device may incorporate a locking mechanism which can be engaged to lock the sealing element into the collapsed position. The device may incorporate a valve to prevent flow through the tubular members, for example to prevent egress of the embolic from a cavity. The device can be detached to provide a permanent seal of the orifice, and can retain the embolic within the cavity. The device may be used in conjunction with a stent or other retention device to assist the sealing element in maintaining the seal.

13 Claims, 5 Drawing Sheets

U.S. PATENT DOCUMENTS

| | | | |
|---|---|---|---|
| 5,423,829 | A | 6/1995 | Pham et al. |
| 5,562,726 | A | 10/1996 | Chuter |
| 5,624,449 | A | 4/1997 | Pham et al. |
| 5,855,578 | A | 1/1999 | Gugliemi et al. |
| 5,891,128 | A | 4/1999 | Gia et al. |
| 5,895,385 | A | 4/1999 | Gugliemi et al. |
| 5,916,235 | A | 6/1999 | Gugliemi |
| 5,925,037 | A | 7/1999 | Gugliemi et al. |
| 5,928,226 | A | 7/1999 | Gugliemi et al. |
| 5,928,260 | A * | 7/1999 | Chin et al. ............... 606/200 |
| 5,935,148 | A | 8/1999 | Villar et al. |
| 5,941,888 | A | 8/1999 | Wallace et al. |
| 5,944,714 | A | 8/1999 | Gugliemi et al. |
| 5,947,962 | A | 9/1999 | Gugliemi et al. |
| 5,947,963 | A | 9/1999 | Gugliemi |
| 5,964,797 | A | 10/1999 | Ho |
| 5,976,126 | A | 11/1999 | Gugliemi |
| 5,984,929 | A | 11/1999 | Bashiri et al. |
| 6,010,498 | A | 1/2000 | Gugliemi |
| 6,036,720 | A | 3/2000 | Abrams et al. |
| 6,063,070 | A | 5/2000 | Eder |
| 6,063,104 | A | 5/2000 | Villar et al. |
| 6,066,133 | A | 5/2000 | Gugliemi et al. |
| 6,077,260 | A | 6/2000 | Wheelock et al. |
| 6,083,220 | A | 7/2000 | Gugliemi et al. |
| 6,086,577 | A | 7/2000 | Ken et al. |
| 6,156,061 | A | 12/2000 | Wallace et al. |
| 6,156,064 | A | 12/2000 | Chouinard |
| 6,165,178 | A | 12/2000 | Bashiri et al. |
| 6,179,860 | B1 * | 1/2001 | Fulton et al. ............... 606/116 |
| 6,193,708 | B1 | 2/2001 | Ken et al. |
| 6,344,041 | B1 | 2/2002 | Kupieck et al. |
| 6,344,048 | B1 | 2/2002 | Chin et al. |
| 6,371,972 | B1 | 4/2002 | Wallace et al. |
| 6,375,669 | B1 | 4/2002 | Rosenbluth et al. |
| 6,383,171 | B1 | 5/2002 | Gifford et al. |
| 6,383,174 | B1 | 5/2002 | Eder |
| 6,397,850 | B1 | 6/2002 | Scheldrup et al. |
| 6,425,893 | B1 | 7/2002 | Gugliemi |
| 6,425,914 | B1 | 7/2002 | Wallace et al. |
| 6,454,780 | B1 | 9/2002 | Wallace |
| 6,468,266 | B1 | 10/2002 | Bashiri et al. |
| 6,635,068 | B1 * | 10/2003 | Dubrul et al. ............... 606/200 |
| 6,994,718 | B2 | 2/2006 | Groothuis et al. |

FOREIGN PATENT DOCUMENTS

| | | |
|---|---|---|
| WO | WO 99/05977 | 2/1999 |
| WO | WO 00/13593 | 3/2000 |
| WO | WO 02/069783 | 9/2002 |

* cited by examiner

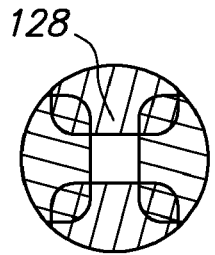
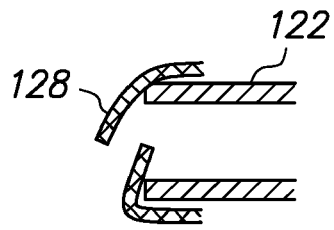
FIG. 16    FIG. 17
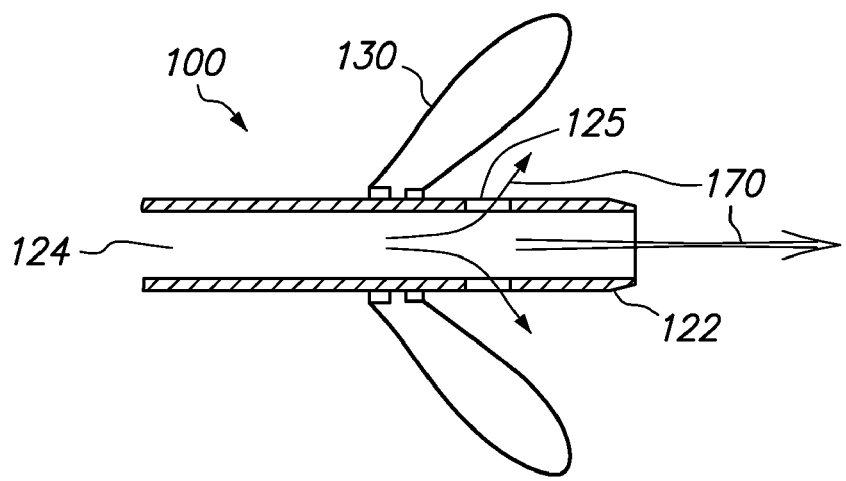
FIG. 18
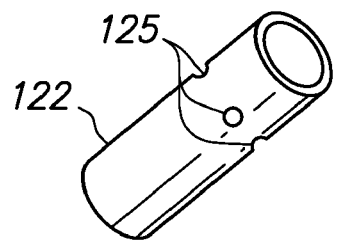
FIG. 19

OCCLUSIVE CINCHING DEVICES AND METHODS OF USE

RELATED APPLICATION DATA

This application is a continuation of U.S. application Ser. No. 10/338,514, filed Jan. 7, 2003, which is hereby incorporated by reference in its entirety.

TECHNICAL FIELD

This invention relates to methods and devices for blocking orifices and occluding cavities within a patient.

BACKGROUND OF THE INVENTION

The present invention deals with a system for treating an aneurysm. More specifically, the present invention deals with a removable occlusion system deployed in the vasculature containing the aneurysm.

Several methods of treating aneurysms have been attempted, with varying degrees of success. For example, open craniotomy is a procedure by which an aneurysm is located, and treated, extravascularly. This type of procedure has significant disadvantages. For example, the patient undergoing open craniotomy must undergo general anesthesia. Also, the patient undergoes a great deal of trauma in the area of the aneurysm by virtue of the fact that the surgeon must sever various tissues in order to reach the aneurysm. In treating cerebral aneurysms extravascularly, for instances, the surgeon must typically remove a portion of the patient's skull, and must also traumatize brain tissue in order to reach the aneurysm.

Other techniques used in treating aneurysms are performed endovascularly. Such techniques typically involve attempting to form a mass within the sac of the aneurysm. Typically, a microcatheter is used to access the aneurysm. The distal tip of the micro catheter is placed within the sac of the aneurysm, and the microcatheter is used to inject embolic material into the sac of the aneurysm. The embolic material includes, for example, detachable coils or an embolic agent, such as a liquid polymer. The injection of these types of embolic materials suffer from disadvantages, most of which are associated with migration of the embolic material out of the aneurysm into the parent artery. This can cause permanent and irreversible occlusion of the parent artery.

For example, when detachable coils are used to occlude an aneurysm which does not have a well defined neck region, the detachable coils can migrate out of the sac of the aneurysm and into the parent artery. Further, it is, at times, difficult to gauge exactly how full the sac of the aneurysm is when detachable coils are being injected. Therefore, there is a risk of overfilling the aneurysm in which case the detachable coils also spill out into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can recanalize.

Embolic agent migration is also a problem. For instance, where a liquid polymer is injected into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Some such techniques, commonly referred to as flow arrest techniques, typically involve temporarily occluding the parent vessel proximal of the aneurysm, so that no blood flow occurs through the parent vessel, until a thrombotic mass has formed in the sac of the aneurysm which helps reduce the tendency of the embolic material to migrate out of the aneurysm sac. However, thrombotic mass can dissolve through normal lysis of blood. Also, in certain cases, it is highly undesirable to occlude the parent vessel even temporarily. Therefore, this technique is, at times, not available as a treatment option. In addition, even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

SUMMARY OF THE INVENTION

Methods and devices for blocking orifices and occluding cavities within a patient are provided. The device comprises first and second tubular members attached at their distal ends to a collapsible sealing element. The device can be placed through an orifice and the collapsible sealing element can be collapsed to seal the orifice. An embolic may be introduced distal to the sealing element to occlude a cavity. The device may incorporate a locking mechanism which can be engaged to lock the sealing element into the collapsed position. The device may incorporate a valve to prevent flow through the tubular members, for example to prevent egress of the embolic from a cavity. The device can be detached to provide a permanent seal of the orifice, and can retain the embolic within the cavity. The device may be used in conjunction with a stent or other retention device to assist the sealing element in maintaining the seal.

BRIEF DESCRIPTION OF THE DRAWINGS

FIGS. 13-17 present views of different valves which may be incorporated into the second tubular member to prevent egress or backflow of an embolic through the device after deployment.

FIGS. 18-19 show a multiport tip which may be incorporated on the distal end of the second tubular member to allow for slow release of a liquid embolic onto the sealing element prior to delivery of the bulk of the embolic into the interior of the cavity to be occluded.

DETAILED DESCRIPTION OF THE INVENTION

Figure 1:
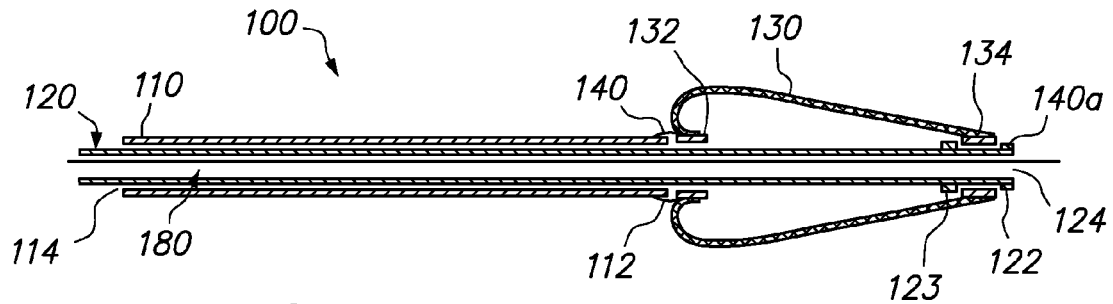
FIG. 1 shows a side view of an occlusive device of the present invention in the extended or nondeployed conformation.
Figure 2:
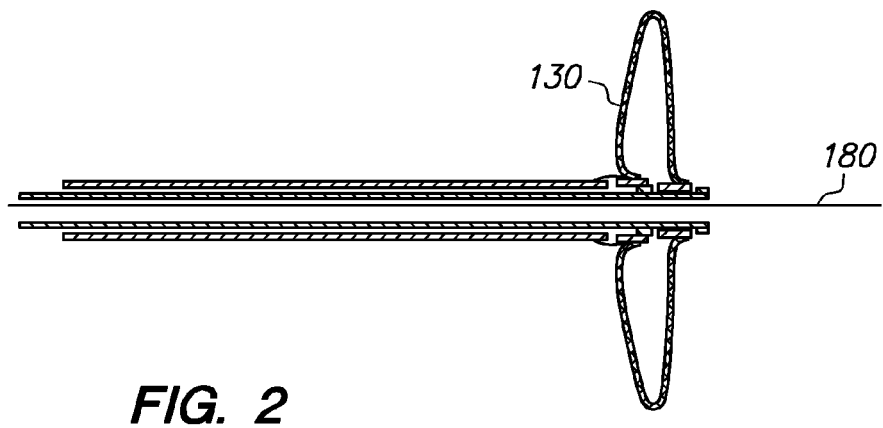
FIG. 2. is a side view of the device of FIG. 1 in the collapsed or deployed position.

Before the present invention is described in detail, it is to be understood that this invention is not limited to the particular methodology, devices or apparatuses described, as such methods, devices or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "an embolic" includes a plurality of embolics, reference to "a locking mechanism" includes a plurality of such mechanisms, and the like.

Terms such as "connected," "attached," "linked," and "conjugated" are used interchangeably herein and encompass direct as well as indirect connection, attachment, linkage or conjugation unless the context clearly dictates otherwise.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

"Optional" or "optionally" means that the subsequently described event or circumstance may or may not occur, and that the description includes instances where the event or circumstance occurs and instances in which it does not.

Methods and devices for blocking orifices and occluding cavities within a patient are provided. An occlusion device 100 comprises first and second tubular members 110, 120 attached at their distal ends 112, 122 to a collapsible sealing element 130. See FIGS. 1-3 and 20-22. Movement of the tubular members relative to one another allows the manipulation of the sealing element to block an orifice.

The tubular members are generally elongate and flexible, to permit their manipulation throughout the body of a patient. Typically the device will be introduced through the vasculature, for example through a leg vein, to treat an aneurysm within a blood vessel. The tubular members have central lumens 114, 124 extending longitudinally therethrough, with the second tubular member 120 located within the lumen 114 of the first tubular member 110. The tubular members are generally axially aligned, and may be coaxial. The second tubular member may substantially occupy the lumen of the first tubular member, or a space may be provided between the tubular members, permitting introduction of a fluid (for example a contrast agent) into the interior of the sealing element 130. Alternatively a catheter may be used to introduce a fluid into the sealing element, where desired, or one or more ports fluidly connected to the interior of the sealing element may be incorporated into the device.

The second tubular member communicates with the interior of the aneurysm, and its lumen can be used for positioning on a guidewire and introducing embolics into an aneurysm or other cavity. In some variations, the second tubular member may be detached prior to introduction of all or some of the embolics, allowing for introduction of larger embolic devices which can be received within the larger lumen of the first tubular member once the second tubular member is removed. Where the second tubular member is detached first and removed, the first tubular member then communicates with the interior of the aneurysm.

The tubular members can be made of any suitable flexible material which can function in the device as described, and may be a composite of materials. Polymeric materials, including copolymeric materials, can be used, for example polytetrafluoroethylene (PTFE), polyether-block co-polyamide copolymers (e.g., PEBAX®), or urethane. Flexible metals can also be used, for example wires such as stainless steel wire, nitinol, etc. Materials can be incorporated to improve kink resistance. Hydrophilic coatings can be added to improve bioacceptability. In one example, a tubular member can comprise an inner layer of PTFE, a stainless steel wire winding, a polymeric layer, and a dip coating of a hydrophilic agent. The tubular members may incorporate visualization or contrast agents; for example, the second tubular member 120 may incorporate a contrast agent 123 allowing determination of the position of the tip during introduction.

The first and second tubular members can be manually positioned individually, or can be connected to a device capable of controlling their movements. The tubular members can incorporate hubs at a proximal end for attachment to such a device. A handle may be included to lock the outer and inner tubular members and thereby prevent the premature deployment of the device during delivery.

The second lumen 124 may be disposed around a guidewire 180 used to guide the introduction of the device into a desired cavity or orifice, or the device may be used without a guidewire. See FIGS. 1-2. Desirably, a radioopaque material may be incorporated into the guidewire, one or both of the tubular members, or all three, to permit visualization of their positions during use.

Unlike other devices, the detachable sealing element described herein requires no unique guidewire that must be specially manufactured, but allows the use of unmodified commercially available guidewires, thereby decreasing costs and simplifying manufacture and operation. The device of the present invention requires no physical attachment to the guidewire, and so can in principle be used with any guidewire of suitable dimensions.

The device advantageously displays a low profile, simplifying introduction of the device and permitting introduction into more remote areas of, for example, the vasculature, then could be reached by a thicker device.

The sealing element is detachably connected at its first and second ends 132, 134 respectively to the first and second tubular members at their distal ends, allowing the sealing element to remain implanted within the orifice once detached. By distal end is meant a position at or near the distal end of a tubular member, and does not preclude the tubular member from extending distally past the point to which the sealing element is attached, such that portions of the tubular members may be included in that part of the device which is detached. In one variation, an extension of the second tubular member beyond the sealing element is included to permit more advanced introduction of an embolic 170 past the sealing element. In another variation, the sealing element includes a catch or lever system 137 at its first end for engagement of the first distal end 112 of the first tubular member by abutment, and is not otherwise connected to the first tubular member. Extension of the first tubular member relative to the second tubular member when this abutment system is engaged causes the cinching or collapse of the sealing element into the deployed shape. See FIGS. 20-22.

Figure 11:
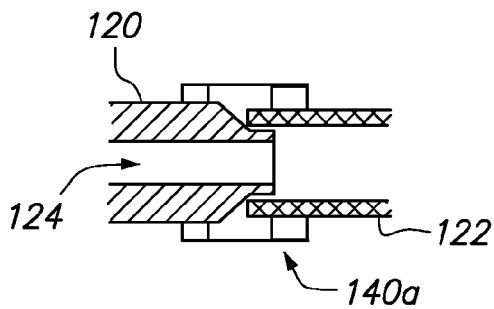
FIGS. 11 and 12 show a magnified side view of the distal end of the second or inner tubular member of the device. An electrolytically detachable link is shown, positioned so that the distal end of the member may be detached. This allows the use of quick-setting liquid embolics which could otherwise harden while still within the end of the inner tubular member and hinder detachment.
Figure 12:
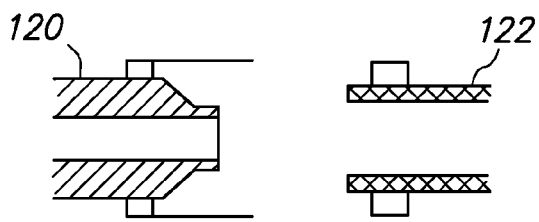

The detachable connections 140, 140a to the first and second tubular members may be of the same type, or may be different. Any form of connection that allows for implantation of the device and that can be detached upon deployment of the sealing element can be used. The connection may be an adhesive connection, a friction fit, a ring and joining rib, a mechanically detachable joint, or an electrolytically detachable joint. Desirably, at least one of the detachable connections is an electrolytic joint constructed of a material that is susceptible to electrolytic dissolution in blood and that dissolves in response to an intentionally timed and applied electrolytic signal. An example of detachment of the second tubular member 120 is shown in FIGS. 11-12. The lumen 124 and the second tubular member can be formed so that the distal end 122 will cleanly separate upon activation of electrolytically detachable connection 140a.

Figure 3:
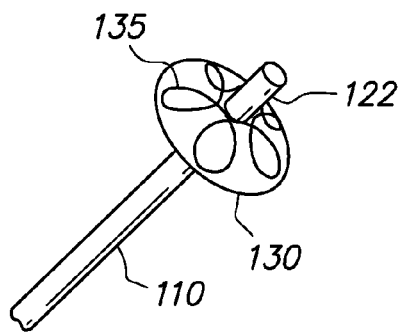
FIG. 3 is a perspective view of the device of FIG. 2 in the collapsed position, demonstrating a disk-like shape suitable for occluding an orifice or aneurysm.

The sealing element 130 can be made of any material suitable for the desired application. The sealing element can be formed of a bio-compatible fabric-like material, such as a braided, woven polymeric material, or a nonwoven polymeric material such as an electrostatically spun membrane for example as described in U.S. Pat. No. 6,156,064 issued Dec. 5, 2000 to Choinard, and Medical Textile Structures: An Overview by Bhupender S. Gupta (Medical Plastics and Biomaterials, January 1998; http://www.devicelink.com/mpb/archive/98/01/001.html). Whether in a fabric-like form or not, the sealing element may comprise one or more polymers, for example polyethylene, polypropylene, polyvinylchloride, a polyamide (e.g., Nylon), polyurethanes, polyvinylpyrrolidone, polyvinyl alchohols, polyvinylacetate, cellulose acetate, polystyrene, polytetrafluoroethylene, a polyester (e.g. polyethylene terphthalate (Dacron)), polyurethane, silk, and cotton. The sealing element can comprise one or more biodegradable or bioabsorbable materials, for example polylactic acid, polyglycolic acid, or a copolymer thereof. (Other elements of the device, embolics and/or stents may comprise such materials as well.) A radio-opaque material 135 can be woven or otherwise incorporated into the sealing element (i.e., tantulum platinum, gold, etc.) to facilitate and assist in guidance through a vascular system utilizing radiography or fluoroscopy. FIG. 3 shows a perspective view of an occlusive device in the collapsed or deployed shape, with the generally disklike sealing element extending generally radially outwards. Radioopaque fiber 135 is shown woven into the sealing element.

Figure 8:
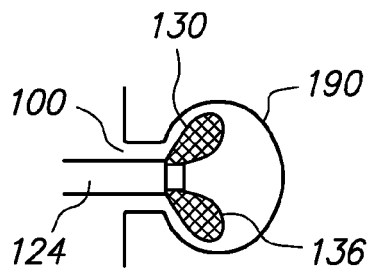
FIGS. 8-10 show an occlusive device in use in occluding an aneurysm. An optional contrast agent is shown within the sealing element of the device. The contrast agent is introduced into the sealing element, causing it to swell and aiding in its visualization. As an embolic is introduced through the device to occlude the aneurysm, the sealing element is compressed, causing the contrast agent to be forced out. This allows the introduction of a non-radioopaque embolic to be monitored.
Figure 9:
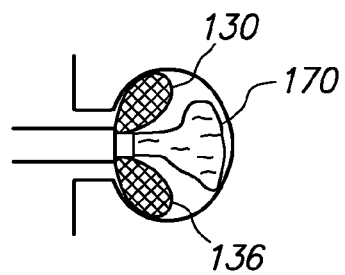
Figure 10:
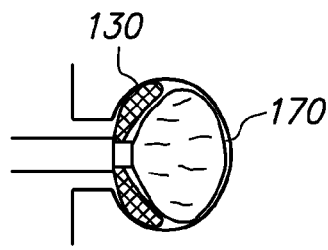

The sealing element can comprise an elastomer, allowing it to be filled with a liquid (e.g. a contrast agent 136) and can expand, and can then be contracted upon introduction of an embolic 170 into the cavity and thereby aid in monitoring of the process. See FIGS. 8-10. Furthermore, the sealing element can comprise or be made entirely of a metallic wire, for example platinum wire or stainless steel wire, which can itself be radioopaque. The sealing element may be formed of a material (e.g., nitinol) capable of assuming a shape memory and may have a predetermined deployed shape. The sealing element may be porous or nonporous. Where porous, the mesh may be preclotted prior to insertion into the cavity using clotting factors which may optionally be obtained from the patient being treated. The sealing element may take the form of a braided tube comprising multiple different materials, which can impart different properties, e.g. polymer yarns, metal wires, radioopaque strands, etc.

The sealing element 130 may assume any generally flattened shape when collapsed. The inherent shape of the collapsed sealing element can be controlled in any of various ways, for example by using combination(s) of different materials to form the element, or by using combinations of materials of different thickness. Typically the sealing element will assume a generally disklike shape in the collapsed shape, which is generally collapsed longitudinally along the axis of the second, or both, tubular members, and extends generally radially outwards therefrom. The tubular member may include one or more folds and/or grooves to cause the sealing element to fold at a predetermined location when collapsed.

The tubular members are disposed so as to retain the sealing element in an extended shape generally extended longitudinally along the axis of the second, or both, tubular members during introduction of the device, and can be moved relative to one another, typically sliding along one another coaxially to expand and contract the sealing element. In some variations, the sealing element may be so maneuvered using the tubular members a number of times during introduction in order to obtain a desirable position. This control scheme in those variations allows for the reversible manipulation of the sealing element while being deployed.

Figure 20:
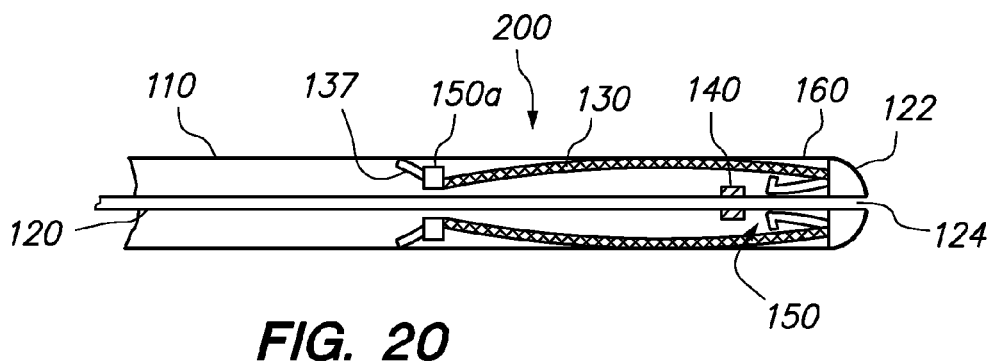
FIGS. 20-22 show a variation of the device in which the first tubular member acts as a sheath for the sealing element during deployment. The first tubular member can then be retracted over the sealing element, releasing a catch on the second end of the sealing element. A distal end of the first tubular member can then engage the catch and collapse or cinch the sealing element into the deployed shape.
Figure 21:
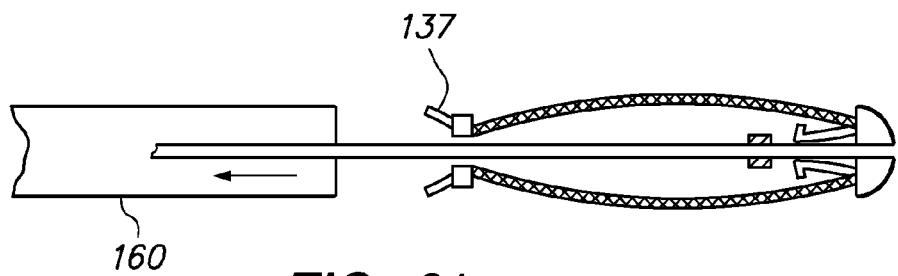
Figure 22:
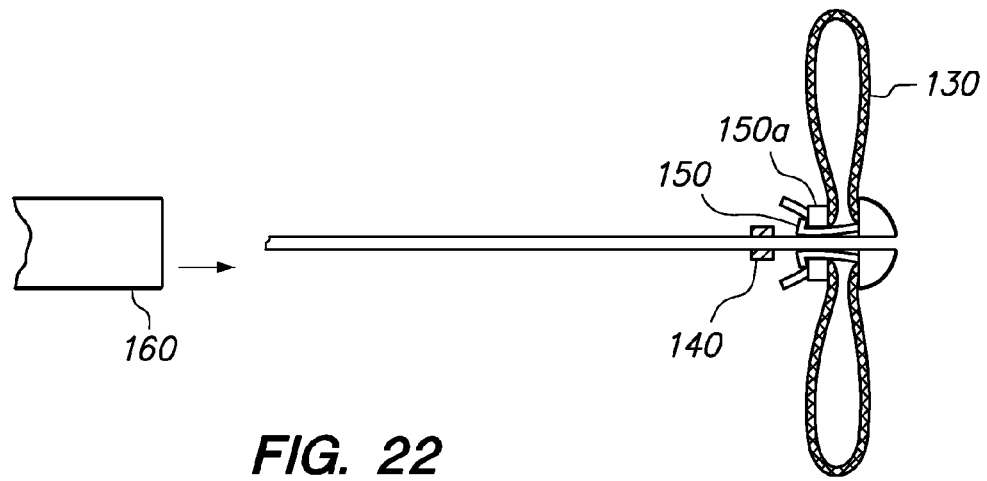

The sealing element can be protected by a retractable sheath 160 that can cover the sealing element during introduction of the device. The sheath can then be retracted in the vicinity of the passage or orifice, exposing the sealing element and allowing its use as a seal. The sheath itself may be used to position the sealing element in certain variations, and the outer tubular member may act as the sheath. As shown in FIGS. 20-22, the sheath 160 (also serving as first outer tubular member 110) protects the sealing element 130 during positioning. The sheath 160 can then be retracted to release the sealing element and catches or levers 137 on the second end of the sealing element. The distal end of the sheath 160 is shaped so that it can engage the catch system 137 and thereby by used to push the second end of the sealing element, comprising locking elements 150a in the variation shown in FIGS. 20-22, into the deployed shape. The sheath 160 can be further pushed to engage the locking system 150, 150a. (Alternatively, the position of the sheath can be maintained in one place engaging the levers while the inner tubular member is pulled or retracted, or both tubular members may be moved.)

The device may incorporate a multiport tip with ports 125 at its distal end 122 for deploying an embolic 170 distal to the device to prevent efflux through the sealing element 130. See FIGS. 18-19. Where the sealing element is a porous material such as mesh, using such a multiport tip, the operator can first introduce a small amount of the embolic to contact the mesh and allow it to harden prior to introduction of a sufficient amount of embolic. A catheter may alternatively be used to introduce a liquid embolic or other agent into the cavity, and may pass through the second lumen 124. The second lumen 124 itself may also be used to deliver the embolic.

Figure 23:
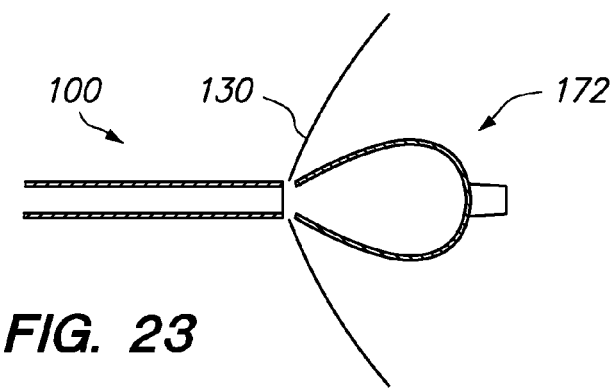
FIG. 23 shows a schematic side view of an occlusive device comprising a tethering element designed to protrude into a cavity and engage an embolic inserted therein to lock the embolic and device together.

Any embolic 170 suitable for occluding a cavity can be used. Exemplary embolics which can be used include hardening agents, coils (e.g. "liquid coils") which may be delivered over a guidewire passing through the device, fibers, particles, supporting members or microspheres, or combinations thereof. The embolic material, as ultimately deployed, must be capable of retention within the cavity by the sealing element being used. The device may comprise a tethering element or elements 172 (FIG. 23) that anchors the embolic to the sealing element, which may extend from the tubular member(s), their lumen(s), and/or the sealing element. The anchoring may take place through any available mechanism, for example through physical entanglement (e.g., where the embolic comprises coils), through entrapment of the element within a hardening embolic, by entrapment within the embolus, or by combinations of mechanisms. In one variation, additional loops of material (e.g. wire, fiber or yarn) may extend from the sealing element towards the distal end of the inner tubular member, which loops will protrude into the cavity upon cinching of the sealing element and be available for entanglement with the embolic. Diffusing tips may be used on the end of the catheter or port used to introduce the embolic and thereby allow the embolic to be deployed evenly.

Figure 4:
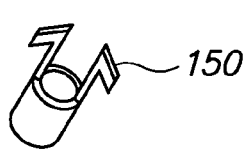
FIG. 4 is a perspective view of one locking mechanism which can be incorporated into the occlusive device to lock it in the deployed shape.
Figure 5:
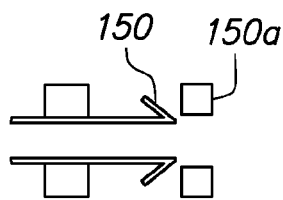
FIGS. 5 and 6 are side views of this locking mechanism in unlocked and locked positions, respectively.
Figure 6:
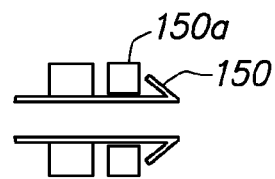

The device may incorporate one or more locking elements 150, 150a tending to fix the sealing element in the deployed shape upon engagement. See, for example, FIGS. 4-6. Any locking mechanism that can lock the sealing element into the deployed shape can be used. Exemplary locking mechanisms suitable for use in the occlusive device include latching systems, dimples, detents including rim and bump-ring systems, friction-fit elements, entanglement systems, and locking barbs (FIGS. 4-6). Entanglement systems can include, for example, hook-and-loop systems for example VELCRO® fasteners), and systems in which a slidable member such as a tube or post passes into a mesh or braid (e.g., nitinol braid) which seals behind the end of the slidable member and prevents its removal. Mechanical expansion elements can be incorporated as locking elements, wherein movement of the tubular members releases an expandible element (for example, a ring or strips) once the tubular members exceed a particular relative offset which prevents return to the extended shape. Engagement of the locking mechanism causes the sealing element to at least strongly resist movement away from the collapsed shape, and may effectively permanently lock the sealing element in that position.

Where the locking mechanism is located on the tubular members, typically the locking elements 150, 150a are located on or near the distal ends 112, 122 of the tubular members, but in principle can be located anywhere on the tubular members that allow them to be locked in a position fixing the sealing element in the deployed shape.

Alternatively or additionally, the locking mechanism 150 can be located within the sealing element 130 itself. For example, hook-and-loop members can be located within the sealing element so that, when the sealing element is moved into the deployed shape, the inner surface of the sealing element, brought into opposition by the movement of the first and second tubular members, is locked into the deployed shape by virtue of attachment of the hooks and loops brought into opposition. Locking mechanisms may be located on the tubular members, on the sealing element, or on the tubular members and the sealing element.

Figure 13:
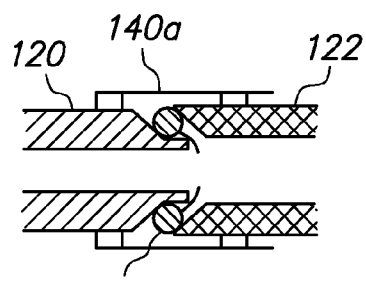
Figure 14:
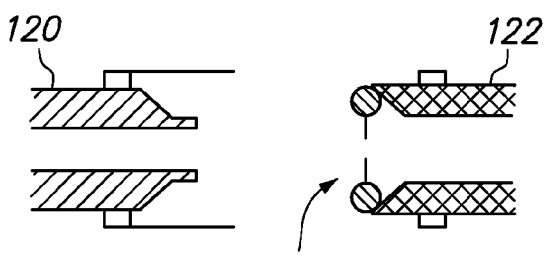
Figure 15:
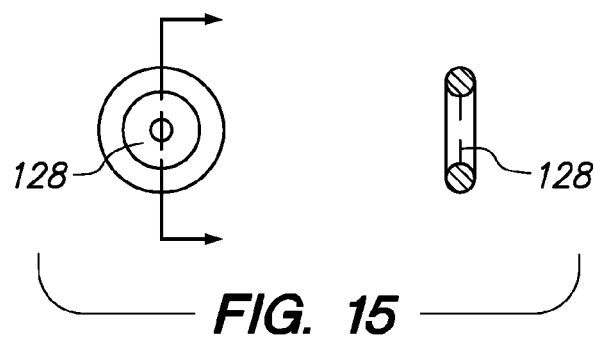

The device may include one or more valves 128 or valve-like elements controlling the passage of fluid through the lumen(s) of the tubular members. See FIGS. 13-17. These valves can be used to prevent egress of an embolic 170 from an aneurysm 190 after occlusion. Any element suitable for sealing the lumen(s) can be employed as a valve. The valves may take the form of flaps (FIGS. 16-17) that are released in conjunction with detachment of the device, or may take the form of an annular seal (FIGS. 13-15) which is similarly released on detachment of the device to seal the lumen. The valves 128 need not only deploy in conjunction with detachment of the device, and their deployment may be separately controllable.

The device may be provided sealed in a package in single use form, and may be provided sterilized for performing a medical procedure using any suitable sterilizing technique, for example using heat, ultraviolet light, radiation, and/or a sterilizing gas (e.g., ethylene oxide). The device may be packaged with a guidewire suitable for use in introducing the device into an orifice or body cavity.

The devices described herein can, in principle, be used for blocking any orifice or for occluding any cavity within the body, limited only by accessibility to the device and by the shape and size of the orifice or cavity. The device may be used to seal an atrial septal defect, or to seal a penetrating wound. The device may be used as a temporary or permanent seal.

Figure 7:
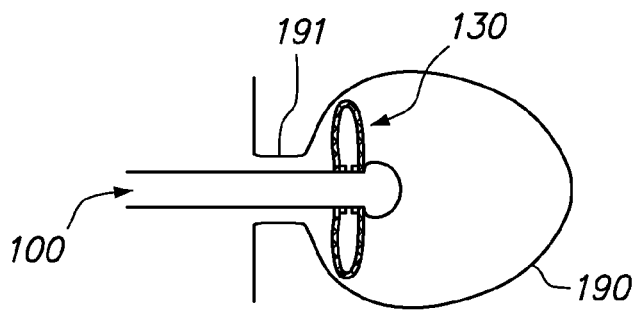
FIG. 7 shows a deployed occlusive device positioned within an aneurysm.

Most typically, the device will be used to seal an aneurysm 190 (FIG. 7), and may be employed with an embolic as described above. The sealing element 130 is positioned within the aneurysm 190 so that it occludes the neck 191. An embolic may then be introduced and the device detached in place. In some variations, the device may be removed after the embolic has hardened or otherwise will maintain an occlusion of the aneurysm or other cavity in the absence of the sealing element 130. A retention device (stent or similar device) may optionally be employed to assist in maintaining the occlusion of the cavity.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

What is claimed is:

1. An occlusive device comprising:
    a first tubular member comprising a first distal end and a first lumen;
    a second tubular member comprising a second distal end and a second lumen, said second tubular member received within the first lumen of the first tubular member;
    a collapsible sealing element adapted to be disposed within a body cavity across a passage thereto, said sealing element having a collapsed shape and an extended shape, said sealing element comprising a first end and a second end, said first end detachably connected to said first tubular member at or near said first distal end, and said second end detachably connected to said second tubular member at or near said second distal end, said extended shape being generally extended longitudinally along the axis of the second tubular member, said collapsed shape being generally collapsed longitudinally along said axis and expanded generally radially outwards therefrom to form a barrier;

said first and second tubular members being longitudinally movable relative to one another to control the movement of the sealing element between the collapsed and extended shapes;

and a locking mechanism, separate from the sealing element, that can be engaged to lock the sealing element in the collapsed shape.

2. A method of blocking an orifice within a patient, comprising introducing the device of claim 1 to said patient, positioning the sealing element to engage the orifice, manipulating the first and second tubular members to move the sealing element into the collapsed shaped blocking said orifice, engaging the locking mechanism to retain the sealing element in the collapsed shape, and detaching the sealing element.

3. A method of occluding a cavity within a patient, comprising introducing the device of claim 1 to said patient, positioning the sealing element within the cavity to be occluded, manipulating the first and second tubular members to move the sealing element into the collapsed shaped blocking an orifice leading to said cavity, and introducing an embolic agent into the cavity to be occluded.

4. The method of claim 3, further comprising detaching the sealing element from the first and second tubular members.

5. The method of claim 3, wherein said cavity is an aneurysm.

6. The method of claim 3, wherein the sealing element is a mesh.

7. The method of claim 6, wherein the embolic is introduced as a liquid and is first introduced into the cavity in a first amount sufficient to contact the mesh but less than is necessary to occlude the cavity, allowing the first amount to harden and thereby block the surface of the mesh, and then introducing a second amount of said embolic sufficient to occlude said cavity.

8. The method of claim 3, wherein the sealing element is a polymer.

9. The method of claim 3, wherein the sealing element is an elastomer.

10. The method of claim 9, wherein the sealing element is filled with a contrast agent to allow determination of its position prior to introduction of the embolic into the cavity.

11. The method of claim 3, wherein said device is introduced using a guidewire passing through said second lumen, wherein said guidewire is not physically attached to said device.

12. The method of claim 3, wherein the embolic comprises a material which anchors the embolic in the sealing element.

13. The occlusive device of claim 1, wherein said locking mechanism comprises one or more hooks, said locking mechanism configured such that said one or more hooks engage said detention ring to lock the sealing element in the collapsed shape.

* * * * *